(12) United States Patent
Sohling et al.

(10) Patent No.: US 7,897,051 B2
(45) Date of Patent: Mar. 1, 2011

(54) METHOD FOR SEPARATING PROTEINS FROM LIQUID MEDIA

(75) Inventors: Ulrich Sohling, Freising (DE); Thomas Scheper, Hannover (DE); Cornelia Kasper, Hannover (DE); Daniel Riechers, Hannover (DE); Arne Burzlaff, Hannover (DE)

(73) Assignee: Sud-Chemie AG, Munich (DE)

( * ) Notice: Subject to any disclaimer, the term of this patent is extended or adjusted under 35 U.S.C. 154(b) by 369 days.

(21) Appl. No.: 12/095,784

(22) PCT Filed: Dec. 15, 2006

(86) PCT No.: PCT/EP2006/012130
§ 371 (c)(1),
(2), (4) Date: Aug. 25, 2008

(87) PCT Pub. No.: WO2007/073893
PCT Pub. Date: Jul. 5, 2007

(65) Prior Publication Data
US 2009/0306346 A1    Dec. 10, 2009

(30) Foreign Application Priority Data
Dec. 16, 2005   (DE) .................. 10 2005 060 392

(51) Int. Cl.
*B01D 15/04*   (2006.01)
(52) U.S. Cl. .................. 210/670; 210/690; 210/691
(58) Field of Classification Search .................. 210/670, 210/690, 691
See application file for complete search history.

(56) References Cited
U.S. PATENT DOCUMENTS
2,454,942 A    11/1948   Pierce et al.

(Continued)

FOREIGN PATENT DOCUMENTS
DE    10356894    7/2005

(Continued)

OTHER PUBLICATIONS
Buttersack, C., et al., "Enzyme Production from Sugar Beets" (English translation).

(Continued)

*Primary Examiner*—Chester T Barry
(74) *Attorney, Agent, or Firm*—Scott R. Cox

(57) ABSTRACT

The invention relates to a method for separating proteins from liquid media, comprising
  providing a liquid medium containing proteins,
  providing a clay material which has:
    a specific surface greater than 150 m$^2$/g,
    a pore volume greater than 0.35 ml/g,
    an ion exchange capacity greater than 40 meq/100 g, and
    a sediment volume in water of less than 15 ml/2 g,
  equilibrating said clay material to a pH of from 3.5 to 9.0,
  treating said liquid medium with the equilibrated clay material, and
  separating the purified, protein-depleted liquid medium from the clay material.

20 Claims, 3 Drawing Sheets

U.S. PATENT DOCUMENTS

Figure 1:
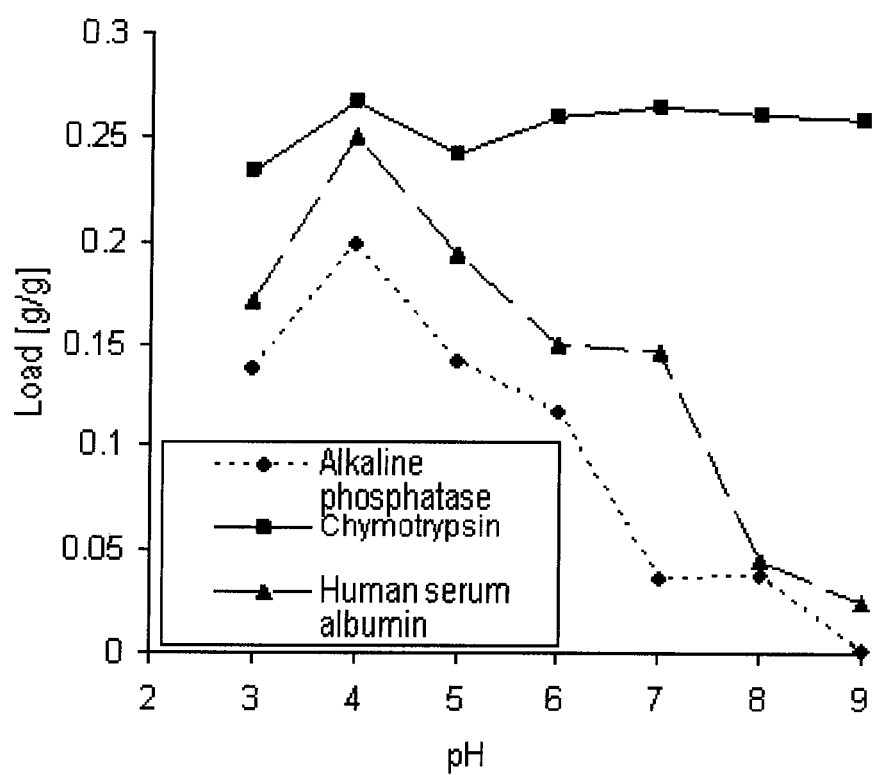

| | | | |
|---|---|---|---|
| 4,029,583 | A | 6/1977 | Ho Chang et al. |
| 4,126,605 | A | 11/1978 | Schneider et al. |
| 4,605,621 | A * | 8/1986 | Pinnavaia et al. ........... 435/177 |
| 4,699,717 | A | 10/1987 | Riesner et al. |
| 5,008,226 | A | 4/1991 | Taylor et al. |
| 5,389,146 | A | 2/1995 | Liao |
| 5,869,415 | A | 2/1999 | Ortiz et al. |
| 7,342,065 | B2 | 3/2008 | Yang et al. |
| 7,351,683 | B2 | 4/2008 | Del Duca et al. |
| 2003/0003272 | A1 | 1/2003 | Laguitton |
| 2006/0276333 | A1* | 12/2006 | Sohling ...................... 502/407 |

FOREIGN PATENT DOCUMENTS

| | | |
|---|---|---|
| DE | 102005012639 A1 | 9/2006 |
| EP | 0071647 A1 | 2/1983 |
| EP | 0180934 | 5/1986 |
| EP | 0281390 A2 | 9/1988 |
| EP | 0635300 A1 | 1/1995 |
| EP | 0987328 A2 | 3/2000 |
| EP | 1162459 A1 | 12/2001 |
| GB | 752669 | 7/1956 |
| GB | 826706 | 1/1960 |
| GB | 938153 | 10/1963 |
| GB | 741663 | 12/1995 |
| IT | 1269857 | 4/1997 |
| JP | 1284310 | 11/1989 |
| KR | 20010085405 A | 9/2001 |
| SU | 878785 | 11/1981 |
| WO | WO9105606 A1 | 5/1991 |
| WO | WO9315832 A1 | 8/1998 |
| WO | WO9902256 A1 | 1/1999 |
| WO | WO0149869 | 7/2001 |
| WO | WO0168798 A1 | 9/2001 |
| WO | WO03098731 A1 | 11/2003 |
| WO | WO2005121791 | 12/2005 |

OTHER PUBLICATIONS

English translation of International Preliminary Report on Patentability pertaining to international application No. PCT/EP2006/012130, filed in the U.S. under U.S. Appl. No. 12/095,784. This application may contain information material to the patentability of the current application.

Alvarez, A.J., et al., "Amplification of DNA Bound on Clay Materials", Molecular Ecology, Blackwell Science, Oxford, GB, Bd. 7, Nr. 6, Jun. 1988, pp. 775-778.

Choy, J., et al., "Inorganic Layered Double Hydroxides as Nonviral Vectors", Angew. Chem. Int. Ed. 2000, 112(22), pp. 4207-4211 (4041-4045).

Khanna, M., et al., "Transformation of *Bacillus subtilis* by DNA Bound on Montmorillonite and Effect of Dnase on the Transforming Ability on Bond DNA", Applied and Environmental Microbiology, Washington, DC, US, Bd. 58, Nr. 6, Jun. 1992, pp. 1930-1939.

Lawson, T.G., et al., "Separation of Synthetic Oligonucleotides on Columns of Microparticulate Silica Coated with Crosslinked Polyethylene Imine", Analytical Biochemistry (1983), 133(1), pp. 85-93.

Lorenz, Michael, "Nucleic Acid Purification by Cation-Complexing", Laborwelt Apr. 2003 [English translation].

English translation of International Preliminary Report on Patentability pertaining to international application No. PCT/EP2005/013236, filed in the U.S. under U.S. Appl. No. 12/096,402. This application may contain information material to the patentability of the current application.

Office Action dated Oct. 14, 2008 with respect to U.S. Appl. No. 10/556,761.

* cited by examiner

METHOD FOR SEPARATING PROTEINS FROM LIQUID MEDIA

The invention relates to a method for separating proteins from liquid media.

Nowadays, biologically active substances are successfully produced on a large scale with the aid of cell culture technology. The established methods enable both enzymes for industrial application, such as for example food production, and pharmaceutically important recombinant proteins to be produced. This involves the target proteins being produced by microorganisms or mammalian cells and then isolated from the culturing medium or the cells. This production process is divided into fermentation with upstream media preparation and a downstream chain of processes serving to purify the target protein. The costs of the protein purification process steps frequently exceed 80% of the total production expenses. Purification usually involves the use of chromatographic methods in order to firstly concentrate the target protein in the process flow and secondly remove foreign proteins and other contaminants such as endotoxins, viruses or DNA. If the chromatographic materials are used several times, they must continually be tested for their separating performance or possible microbial contamination. Validation and purification costs may partially be reduced by using disposable materials. In order to be employed successfully, such disposable chromatographic material must reproducibly produce a high separating performance and require low investments per unit consumed. It should have high binding capacities and rapid binding kinetics for the target proteins of interest or the interfering contaminations.

Bentonites, and more specifically their major mineral component, montmorillonite, are suitable for reversible binding of proteins. Bentonites and other comparable sheet silicates here act as natural cation exchangers and can adsorb proteins at pH values below their isoelectric point. Sodium bentonite, however, has the property of swelling substantially in water. Introducing a few grams of sodium bentonite into an aqueous solution results in a large increase in viscosity, making handling of the liquid media much more difficult. Furthermore, the use of sodium bentonite as filter medium or as packing in a chromatographic column is very complicated, since the substantial swelling greatly increases the volume of the filter packing or column packing, thereby blocking the filter or the column. Therefore the only possible industrial application up to now comprises adding the sodium bentonite in each case batchwise to the liquid medium to be purified and, after adsorption of the proteins, removing said bentonite again by filtration or removing the purified liquid medium by pressing it off the bentonite.

C. Buttersack, K. Novikow, A. Schaper and K. Buchholz (Zuckerind. 119 (1994), No. 4, pp. 284-291) report the use of sheet silicates for separating enzymes from the filtered sap of homogenized sugar beets. Pure enzymes were removed in a simple manner by way of adsorption to sodium bentonite and subsequent desorption using a pH buffer. The studies demonstrate that sheet minerals are well suited to remove or concentrate proteins. However, handling these sheet minerals is complicated because they greatly increase the viscosity of the suspension in water, with said sheet minerals disintegrating to give very small particles. It is therefore very difficult to concentrate proteins by way of packing the sheet material into a column through which the protein-containing liquid is then passed. Without aid measures, the column is blocked relatively quickly because the sheet mineral swells substantially. In order to nevertheless enable the enzymes to be removed in a column, the authors propose embedding the sodium bentonite in a calcium alginate gel. The hydrogenated homogenate is pumped through the column at pH=5.0, which column is filled with beads of the immobilized bentonite. After the nonadsorbed fraction has left the column, the enzyme is eluted with a buffer solution adjusted to pH=8. Due to the high costs arising, the use of sodium bentonite fixed in a calcium alginate, as described by the authors, is less suitable for industrial removal of proteins.

DE 1 160 812 A1 describes a method for increasing protein stability of beer, using a wide-pore silica gel as adsorbent. The beer is treated with a finely ground silica gel which has a surface of from 200 to 400 $m^2/g$, a pore volume of more than 0.6 ml/g and a pore diameter of more than 60 Å.

GB 752,669 describes a method for separating silicon-containing contaminants from solutions containing insulin. During production of insulin, the latter can be separated from organic solutions by adsorbing it to silicon dioxide or to a clay so as to enable the solvent to be removed. Said insulin can then be eluted again using a strongly alkaline aqueous solution. Due to the strongly alkaline pH, however, the aqueous insulin solution is contaminated by silicon-containing contaminants detaching from the adsorbent. Said contaminants are colloidal, thus making their removal by filtration difficult. To remove these contaminants, it is proposed to adjust the aqueous solution to a pH of from 6.5 to 9.0 and subsequently leave it. A precipitate forms which can readily be removed by filtration.

U.S. Pat. No. 4,605,621 describes a method for immobilizing enzymes, wherein the enzyme is reacted with an organically modified clay. The clay used is a smectite, hectorite or vermiculite, in which clay at least part of the cations has been replaced with onium ions and/or organometallic cations, providing the clay with hydrophobic properties.

U.S. Pat. No. 4,126,605 describes a method for preparing γ-globulins, wherein fractions of γ-globulins obtained from blood plasma are purified further. For this purpose, the γ-globulin is first taken up in an aqueous solution containing a hydrocolloid such as hydroxyethyl starch, gelatine, dextrose or albumin and adjusted by a buffer to a pH in the range from 3.5 to 8.0. This solution may be purified further by mixing it with a suspension of a clay mineral. Clay minerals which may be used are, for example, bentonite or vermiculite. By adding an organic solvent, for example a polyethylene glycol, in an amount of about 10% by weight a first fraction is precipitated which essentially contains contaminants. Said fraction can be removed, for example, by centrifugation. More organic solvent up to a proportion of from 16 to 24% by weight is then added at a pH of from about 7.0 to 7.2. In the process, a very pure fraction of γ-globulins precipitates which may then be removed, for example by centrifugation.

EP 0 071 647 A1 describes a method for separating interferons from aqueous solutions. For this purpose, the solution is mixed with a composition containing silicic acid. An example of such a composition which may be used is bentonite, an acid clay, kaolin or a magnesium aluminum silicate. The interferon is adsorbed by the composition and can be eluted with an aqueous solution containing a nonionic surfactant. Examples of suitable surfactants are sorbitan monoalkyl esters, polyalkyl ethers or polyoxyethylene-polyoxypropylene copolymers.

Recently, a new class of clay materials has been found which have very good properties regarding adsorption of biomolecules. These materials, like the clays used previously, are weathered products. However, they no longer exhibit any crystalline properties and are therefore X-ray amorphous. Compared to the clays previously used, they have a very high proportion of $SiO_2$ and a very high pore volume. They do not swell in water, in contrast to sodium bentonites, for example. DE 10 2005 012 639 A1, published after the priority date of the present application, describes a method which makes use of such a clay material for separating interfering biomolecules from liquid media. Thus, for example, said clay material is suitable for clarifying wine or for stabilizing beer.

It was the object of the present invention to provide a method which can be used, even on an industrial scale, for successfully separating proteins from liquid media, and, in a preferred embodiment, it should also be possible to recover the removed proteins without the latter suffering from an undue loss of activity.

The object is achieved by a method having the features of claim 1. Advantageous developments of the method of the invention are subject matter of the dependent claims.

The method of the invention separates proteins from liquid media by:
providing a liquid medium containing proteins,
providing a clay material which has:
a specific surface greater than 150 m$^2$/g,
a pore volume greater than 0.35 ml/g,
an ion exchange capacity greater than 40 meq/100 g, and
a sediment volume in water of less than 15 ml/2 g,
equilibrating said clay material to a pH of from 3.5 to 9.0,
treating said liquid medium with the equilibrated clay material, and
separating the purified, protein-depleted liquid medium from the clay material.

Surprisingly, a clay material having the above-described properties was found to be able to bind proteins in quantities which are interesting in terms of industrial application. Equilibration of said clay material to a pH of from 3.5 to 9.0 prevents irreversible deactivation or denaturation of the proteins adsorbed to the clay material, thereby enabling said proteins to be recovered, where appropriate, without having to accept a substantial loss of their activity. Said equilibration is preferably carried out in such a way that the clay material is treated with a buffer having a pH at which the protein of interest is also stable and does not suffer excessive deactivation. Preference is given to using, for said equilibration, a buffer which is subsequently also used for purifying the liquid medium or the protein of interest. Said buffer is preferably adjusted to about the same pH that has been adjusted in the liquid medium. The equilibration time depends, for example, on the amount of the clay material or, if said clay material is provided in the form of a packing or column, on the dimensions thereof. If the columns are very small, the equilibration time may, where appropriate, be only a few seconds, while very large columns or filter packings may also require longer time periods. The equilibration is carried out preferentially for at least 10 seconds, preferably at least 30 seconds, particularly preferably 1 to 60 minutes. Preference is given to the equilibration being carried out using a buffer solution to which the liquid medium to be purified or the protein to be purified has not yet been added.

A further advantage is the clay material used in the method of the invention having a low sediment volume of less than 15 ml/2 g, preferably less than 10 ml/2 g, i.e. said material swells only negligibly in water. Due to the low swelling of the clay material, the liquid medium to be purified and containing the proteins does not show a substantial increase in viscosity upon addition of said clay material to it. It is furthermore possible to introduce relatively large amounts of the clay material into the liquid medium, so that the proteins of interest can be separated without problems even from media having a high concentration of said proteins. The clay material used may also be separated without problems from the liquid medium by filtration. The clay material does not block the filter, due to the low swelling capacity. As a result, only a comparatively low pressure is required when filtering off the protein-depleted liquid medium.

The liquid medium used may in principle be any liquid which is derived from a biological source or contains proteins. The method is particularly suitable for processing reaction mixtures from bioreactors, in order to remove and concentrate the biologically active substances of interest from large liquid volumes. Another possible use is, for example, the separation of proteins from body fluids such as urine or other biological samples. This enables proteins to be separated and purified quickly from samples of body fluids, for example. For this purpose, the sample, for example a body fluid or another protein-containing sample, is added to the clay material which has been equilibrated to a suitable pH beforehand. The proteins are adsorbed to the clay material, while the liquid phase can be removed. The clay material may then be rinsed, preferably using a buffer solution whose pH corresponds approximately to the pH to which the protein-containing liquid medium has been adjusted prior to application to the clay material. This enables contaminants to be washed out, while the protein remains adsorbed to the clay material and is thereby purified further. After the rinsing step, the protein may be eluted and will then be in a concentrated form.

Where appropriate, the samples must be prepared in the usual manner, for example by carrying out a coarse filtration or by buffering the sample. The sample is preferably buffered to a pH which has also been adjusted during equilibration of the clay material. Sample preparations of this kind are known to the skilled worker. The clay material used in the method of the invention presumably acts as a cation exchanger, with alkali metal or alkaline earth metal ions being released from the clay material and replaced with proteins. Proteins comprise charged amino acid residues on the protein surface which are able to interact with charged groups on the surface of the clay material. The net charge of a protein is the result of the pH of the solution surrounding said protein and of the pI of said protein. The pI of a protein corresponds to the pH at which the net charge of said protein equals zero. The pI is the result of the amino acid composition and the tertiary structure of the protein. In the acidic pH range, the amino acids (preferably the strongly basic amino acids arginine, lysine and histidine) are protonated, and the protein exhibits a cationic character. In the basic pH range, the acidic groups aspargine and glutamine carry negative charges, and the protein is an anion. The interaction between protein and the clay material is low close to the isoelectric point and increases with increasing difference between pH and pI. Preference is therefore given to adjusting the medium to a pH which differs by at least one unit from the isoelectric point of the protein to be removed. If, for example, the protein has a pI of 5.5, it is isolated preferably at a pH below approximately 4.5.

The clay material used in the method of the invention has a pore volume greater than 0.35 ml/g, preferably greater than 0.5 ml/g (determined by the BJH method (cumulative pore volume for pores having a diameter in the range from 1.7 to 300 nm)), a specific surface (BET surface) greater than 150 m$^2$/g, preferably greater than 180 m$^2$/g, particularly preferably more than 200 m$^2$/g, and an ion exchange capacity greater than 40 meq/100 g. The clay material is also characterized by a very low swelling capacity. The swelling volume corresponds preferably to the sediment volume. Suitable analytical methods for determining the pore volume, the specific surface, the ion exchange capacity and the swelling volume are specified in the examples hereinbelow.

Particular preference is given to using clay materials whose ion exchange capacity is greater than 40 meq/100 g, preferably in the range from 45 to 75 meq/100 g. The clay material preferably has a specific surface (BET) in the range from 150 to 280 m$^2$/g, particularly preferably in the range from 170 to 260 m$^2$/g. The pore volume of the clay material used is preferably in the range of greater than 0.35 ml/g, preferably greater than 0.5 ml/g, particularly preferably in the range from 0.7 to 1.1 ml/g, and very particularly preferably in the range from 0.80 to 1.0 ml/g.

As explained hereinabove, the clay material used in the method of the invention swells only to a very small extent, causing no problems with regard to an increase in the viscosity of an aqueous suspension, as is generally observed with sodium bentonite, for example. After the clay material has been left in water at room temperature for three days, the sediment volume is preferably less than 15 ml/2 g, preferentially less than 10 ml/2 g. Room temperature means a temperature of about 15 to 25° C., in particular about 20° C.

Preferred clay materials used are naturally occurring, naturally active or not naturally active clay materials which preferably have not undergone any chemical modification, more specifically have not been dealuminated with strong acids. The clay materials may, where appropriate, be dried and ground to a suitable particle size. The skilled worker arrives at the particle size from the intended application.

Synthetically produced clay materials having the properties specified above may also be used in principle aside from the naturally occurring clay materials. Such clay materials may be produced, for example, from waterglass and a suitable sheet silicate such as bentonite. However, preference is given to using clay materials derived from natural sources.

Particular preference is given to using clay materials whose aluminum content is less than 11% by weight, based on the anhydrous clay material calculated as $Al_2O_3$. The aluminum content is preferably greater than 2% by weight, particularly preferably greater than 4% by weight, especially preferably greater than 6% by weight. The aluminum content is particularly preferably in the range from 8 to 10% by weight. Clay materials obtained by extraction with strong acid exhibit a lower $Al_2O_3$ content than the clay material used in the method of the invention.

Particular preference is given to using clay materials which have only low crystallinity, i.e. are not classified per se to the class of sheet silicates. Said low crystallinity can be determined by X-ray diffractometry, for example. The particularly preferred clay materials are substantially amorphous, i.e. their X-ray diffractograph does not show any sharp peaks. As a result, they do not belong to the class of pure attapulgites or smectites.

Without wishing to be bound by this theory, the inventors assume the clay material used in the method of the invention to comprise a skeleton made of silica gel. A sheet silicate is embedded in this relatively rigid skeleton. By being anchored in the silica gel skeleton, the sheet mineral is able to swell greatly, without greatly increasing its total volume. The swelled sheet silicate is then available to a large extent for adsorption of proteins. The silica gel is the major phase, while the clay phase forms the smaller portion of the clay material. The clay material is presumably responsible for the cation exchange capacity.

In a preferred embodiment, the clay material used in the method of the invention has a particular pore radius distribution. The pore volume of the clay material is produced here substantially by pores having a diameter of at least 14 nm.

Particularly preferably, at least 40% of the total pore volume (determined by the BJH method, cf. hereinbelow) are produced by pores of greater than 14 nm in diameter. Preference is given to more than 50%, and particularly preferably more than 60%, of the total pore volume being produced by pores of greater than 14 nm in diameter. The pore radius distribution or total pore volume is determined by nitrogen porosimetry (DIN 66131) and evaluation of the adsorption isotherms by the BJH method (cf. hereinbelow).

To prevent the protein from denaturing, the clay material is equilibrated to a pH of from about 3.5 to 9.0, particularly preferably 4.0 to 6.0, prior to applying the liquid medium. For this purpose, the clay material is suspended in a suitable buffer, for example a citrate buffer, or such a buffer as applied to a filter packing or column prepared from said clay material for example. The buffer here preferably has a concentration in the range from 30 to 100 mmol/l.

According to another embodiment, the clay material may also be activated prior to removal of proteins by treating it with a sodium-containing compound, for example soda, or a potassium-containing compound, for example potassium carbonate. As a result, the divalent cations of the clay material are replaced partially, or preferably completely, with sodium ions. The divalent ions are replaced with sodium ions in the usual manner, as it is known also from the activation of calcium bentonites. The wet clay material which has a wet content of preferably between 10 and 70% by weight, preferentially 45 to 65% by weight, is kneaded with an amount of soda corresponding to from about 1.2 to 2.5 equivalents of the cation exchange capacity of the clay material. Alternatively, the soda may also be sprayed in the form of a solution on the clay material. The clay material may then be dried and, where appropriate, ground. Said activation can further increase the capacity of the clay material for adsorbing proteins.

In the simplest case, the protein-containing liquid medium may be treated in such a way that the clay material is added to the liquid medium directly or in the form of a suspension and, after an incubation time, preferably in the range from 1 to 30 minutes, particularly preferably 5 to 20 minutes, may be separated from said liquid medium by suitable methods such as, for example, filtration or centrifugation, thereby depleting said medium of proteins.

According to another embodiment, the proteins may be removed by passing the liquid medium through a filter packing which at least partially is formed by the clay material. The filter packing may have in principle any form. Suitable are, for example, filter cartridges filled with the clay material. The filter cartridge may be replaced with a new cartridge, once its absorptive capacity has been exhausted. The filter cartridge loaded with the proteins may either be discarded or preferably subjected to a work-up process in which the proteins adsorbed to the clay material are recovered.

According to one embodiment, the filter packing is prepared by precoat filtration. This involves mixing the clay material preferably with a filter aid such as kieselguhr or Perlit®. The clay material may also be mixed with a further adsorbent such as silica gel. During filtration, the clay material together with the filter aid and, where appropriate, further adsorbents forms a filter cake which forms the filtration-active medium for subsequent turbid matter and filter aid particles. This embodiment is particularly suitable if proteins are to be removed as interfering substances from the liquid medium.

Preference is given to applying, prior to direct filtration, a filter aid layer as primary layer to a filter means. An example of a filter means which may be used is a screen with a suitably narrow mesh. An example of a filter aid which may be used for forming a primary layer is kieselguhr. This process is also referred to as preliminary precoating. In the subsequent filtration phase, further filter aid comprising according to the invention the above-described clay material is added to the suspension. Said filter aids form together with the turbid matter particles a filter cake which is referred to as secondary layer.

According to another embodiment of the method of the invention, said method is carried out by way of chromatography. This involves packing the clay material into a chromatography column and applying the liquid medium from which the proteins are to be separated to the column. An eluent may then pass through the column, enabling the proteins to be fractionated into different fractions due to adsorption effects. This is particularly interesting for removing proteins generated in bioreactors.

This demonstrates the advantages of the clay material used in the method of the invention, which material is distinguished by a very low swelling capacity.

In order to be able to use the clay material according to the invention in a column packing, it is expedient to adjust said material to suitable particle sizes by screening. Particular preference is given here to removing in particular the fine parts of the clay material.

The clay material is adjusted to a particle size of preferably >10 μm, in particular >20 μm, particularly preferably >30 μm, in particular in a range from 40 to 300 μm. Particularly preferably, the clay material has a dry screening residue of >95% of the initial weight on a 45 μm mesh screen, a dry screening residue of >80% on a 63 μm mesh screen, and a dry screening residue of >30% on a 150 μm mesh screen.

The method of the invention is preferably used for obtaining proteins from liquid media. For this purpose, the protein is adsorbed to the clay material and, where appropriate, purified by further rinsing steps and then eluted again from the clay material. The proteins adsorbed to the clay material may be eluted by various methods. For example, the protein may be displaced from the binding sites of the clay material by increasing the salt concentration. It is also possible to adjust the pH of the solution used for elution in such a way that the charge of the adsorbed protein is modified, and the latter is therefore no longer bound by the clay material. If the clay material provided for separating the protein from the liquid medium is in the form of a column through which the liquid medium is passed, the adsorbed protein may be eluted, for example, by passing a salt gradient through the column in such a way that different proteins are eluted at different salt concentrations, i.e. the adsorbed proteins are fractionated. Proteins are bound to the clay material used in the method of the invention inter alia by electrical interactions and/or van der Waals forces. Elution using a high salt concentration buffer reduces the electrostatic interactions between the clay material which acts as a cation exchanger and the protein. Said protein can therefore be detached and eluted from the clay material.

In a further embodiment, the bound proteins are eluted by changing the pH. In this case, the pH of the eluent is different from that of the liquid medium.

For example, proteins may be applied at a pH at which they are in a charged form. The pH of the solution is then preferably adjusted in such a way that it is below the isoelectric point of the protein, i.e. the protein has a positive overall charge. The proteins are bound due to the cation exchanger action of the clay material. The clay material used in the method of the invention thus acts as a cation exchanger material. If the pH is then increased to such an extent that the isoelectric point of the protein is reached or exceeded, the protein, in most cases, has a negative overall charge. Said protein is therefore detached again from the clay material and can be eluted.

Where appropriate, the eluent may be admixed with glycerol or polyglycols. These compounds have very high affinity for the clay material and can therefore facilitate detachment of the protein from the clay material.

Preference is given to the liquid medium comprising water as solvent.

The clay material used in the method of the invention may be used alone or else in combination with a further adsorptive material. The further adsorptive material is preferably selected from the group consisting of silica gel, cellulose and polyvinylpyrrolidone.

The clay material and the further adsorptive material are preferably in a ratio of between 1:10 and 10:1. Depending on the intended application, however, it is also possible to use ratios outside the specified range.

The clay material used in the method of the invention has a very high water-carrying capacity but remains flowable nevertheless. The clay material has a water content of preferably more than 30% by weight, in particular more than 40% by weight, particularly preferably more than 50% by weight.

Figure 2:
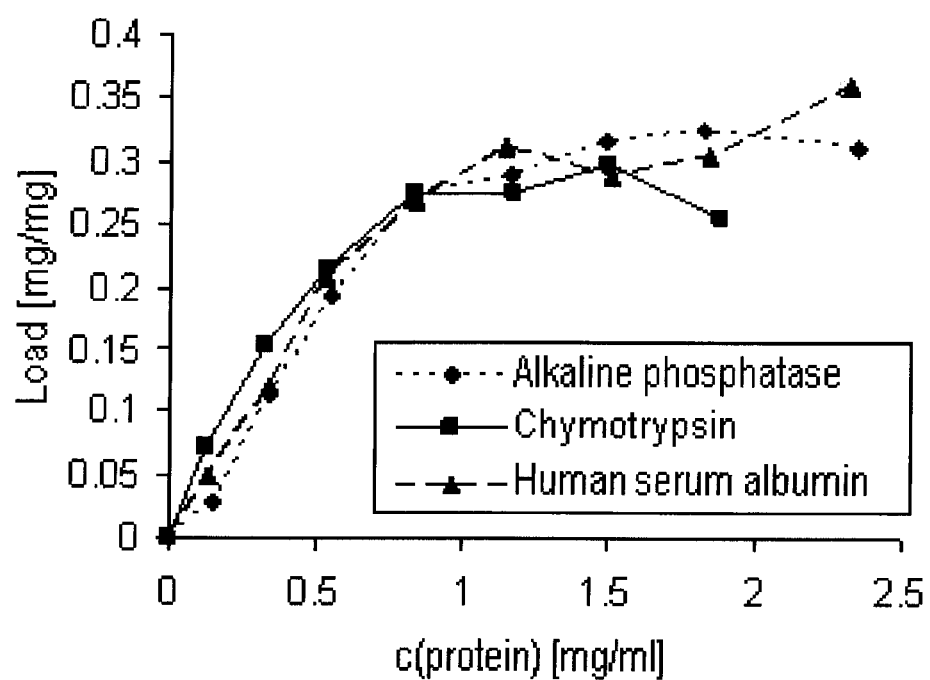
Figure 3:
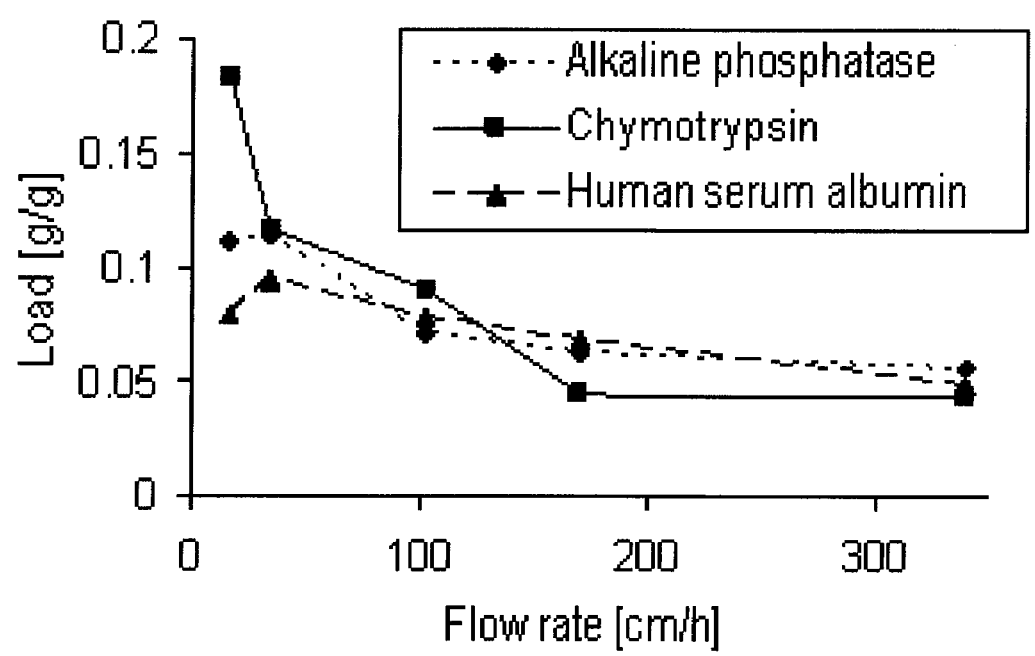

The method of the invention is illustrated in more detail on the basis of the following examples and with reference to the attached figures in which:

FIG. 1: depicts a graph which shows the adsorption of model proteins to the clay material used in the method of the invention as a function of the pH;

FIG. 2: depicts adsorption isotherms of various model proteins to the clay material used in the method of the invention, recorded in a 50 mM citrate buffer; and FIG. 3: depicts a graph which shows the load of the clay material used in the method of the invention as a function of the rate of application of various model proteins.

ANALYTICAL METHODS

Surface/Pore Volume

The surface of the clay materials was performed on a fully automated nitrogen porosimeter from Micromeritics, type ASAP 2010, according to DIN 66131. The pore volume was determined using the BJH method (I. P. Barrett, L. G. Joyner, P. P. Haienda, J. Am. Chem. Soc. 73 (1951), 373). Pore volumes of particular pore size ranges are determined by adding up incremental pore volumes obtained from evaluating the adsorption isotherms by BJH. The total pore volume according to the BJH method refers to pores of 1.7-300 nm in diameter.

Water Content:

The water content of the products at 105° C. was determined using the DIN/ISO 787/2 method.

Elemental Analysis:

This analysis is based on total disaggregation of the clay materials or of the corresponding product. After the solids have dissolved, the individual components are analyzed and quantified by specific analytical methods such as ICP, for example.

Ion Exchange Capacity:

The cation exchange capacity is determined by drying the clay material to be examined at 105° C. for 2 hours. The dried clay material is then refluxed with an excess of an aqueous 2N $NH_4Cl$ solution for one hour. The mixture is left at room temperature for 16 hours and then filtered, followed by washing, drying and grinding the filter cake, and determining the NH$_4$ content in the clay material by nitrogen determination (CHN analyzer from Leco) according to the manufacturer's instructions. The proportion and type of the metal ions exchanged is determined by ICP-AES spectroscopy in the filtrate.

X-ray Diffractometry:

X-ray imaging was carried out using a high resolution powder diffractometer from Phillips (X'-Pert-MPD(PW 3040)) equipped with a Cu anode.

Determination of the Sediment Volume:

A 100 ml graduated measuring cylinder is filled with 100 ml of distilled water. Using a spatula, 2 g of the substance to be measured are applied slowly and in portions of in each case about 0.1 to 0.2 g to the surface of the water. Another portion is added after the previous portion has sedimented. After said 2 g of substance have been added and sedimented to the bottom of the measuring cylinder, the latter is left at room temperature for 1 hour. The height of the sediment volume in ml/2 g is then read from the graduation of the measuring cylinder. To determine the sediment volume after three days of storage in water, the sample mixture is sealed with Parafilm® and left vibration-free at room temperature for three days. The sediment volume is then read from the graduation of the measuring cylinder.

Determination of the Dry Screening Residue:

About 50 g of the air-dried clay material to be examined are weighed out on a 45 μm mesh screen. The screen is connected to a vacuum cleaner which sucks all parts that are finer than the screen through said screen via a suction slit circulating underneath the bottom of the screen. The screen is covered with a plastic lid and the vacuum cleaner is switched on. After five minutes, the vacuum cleaner is switched off and the amount of the coarser parts remaining on the screen is determined by difference weighing.

Determination of the Wet Screening Residue:

First, a 5% strength suspension is prepared by stirring a corresponding amount of the clay material to be examined into water at approx. 930 rpm for approx. five minutes. The suspension is stirred at approx. 1865 rpm for another 15 minutes and then poured through a screen of the desired mesh. The residue is washed with tap water until the run-off is clear. The screen with the residue is then placed into an ultrasonic bath for five minutes to remove remaining fine parts. The remaining residue is briefly washed with tap water, and the ultrasonic treatment is repeated, where appropriate, until no further fine matter passes into the water during said ultrasonic treatment. The screen is then dried to constancy of weight. The residue remaining on the screen is transferred to a weighed porcelain dish for weighing.

Characterization of the Clay Materials:

a) Clay Material A:

A clay material suitable for the method of the invention (Tonsil® EX 1221 I; Süd-Chemie AG, Moosburg, DE, (Rohtonlager Res. No.: 03051)) was examined with respect to its physicochemical properties. The results obtained are summarized in Table 1.

TABLE 1

| Physicochemical analysis of clay material A | |
|---|---|
| Specific surface (m$^2$/g) | 219 |
| Pore volume[1] (ml/g) | 0.881 |
| IUF (meq/100 g) | 52 |

TABLE 1-continued

| Physicochemical analysis of clay material A | |
|---|---|
| Elemental analysis: | |
| SiO$_2$ (% by weight) | 70.6 |
| Fe$_2$O$_3$ (% by weight) | 2.8 |
| Al$_2$O$_3$ (% by weight) | 9.8 |
| CaO (% by weight) | 1.4 |
| MgO (% by weight) | 4.1 |
| Na$_2$O (% by weight) | 0.26 |
| K$_2$O (% by weight) | 1.5 |
| TiO$_2$ (% by weight) | 0.25 |
| Loss at red heat (2 h 1000° C.) | 7.9 |
| Total (% by weight) | 98.6 |

[1] cumulative pore volume according to BHJ for pores of between 1.7 and 300 nm in diameter.

The silicate of the invention was screened to particle sizes of >45 μm, in order for it to be in a form which can be readily packed into columns. The screened material had a dry screening residue of >95% on a 45 μm mesh screen. The dry screening residue was 85% on 63 μm and 30% on 150 μm.

The clay material characterized in table 1 was examined further for the pore volume proportion generated by pores having particular radii. The corresponding data are summarized in tables 2a to c.

TABLE 2a

| | Relative pore volume proportions of pores | | | | |
|---|---|---|---|---|---|
| Range | 0-75 Å | 0-140 Å | 0-250 Å | 0-800 Å | >800 Å |
| Proportion (%) | 10.3 | 19.3 | 34.1 | 78.0 | 22.0 |

TABLE 2b

| | Relative pore volume proportions of pores | | | | |
|---|---|---|---|---|---|
| Range | 0-75 Å | 75-140 Å | 140-250 Å | 250-800 Å | >800 Å |
| Proportion (%) | 10.3 | 9.0 | 14.8 | 43.9 | 22.0 |

TABLE 2c

| | Relative pore volume proportions of pores | | | | |
|---|---|---|---|---|---|
| Range | 0-75 Å | 75-800 Å | >75 Å | >140 Å | >250 Å | >800 Å |
| Proportion (%) | 10.3 | 67.7 | 89.7 | 80.7 | 65.9 | 22.0 | b) Clay Material B:

The physicochemical properties of another clay material suitable for carrying out the method of the invention are summarized in table 3.

TABLE 3

| Physicochemical analysis of clay material B | |
|---|---|
| Specific surface (m$^2$/g) | 198-206 |
| Pore volume[1] (ml/g) | 0.402 |
| IUF (meq/100 g) | 62 |

TABLE 3-continued

Physicochemical analysis of clay material B

Elemental analysis:

| | |
|---|---|
| SiO$_2$ (% by weight) | 35.2 |
| Fe$_2$O$_3$ (% by weight) | 0.93 |
| Al$_2$O$_3$ (% by weight) | 4.6 |
| CaO (% by weight) | 15.4 |
| MgO (% by weight) | 16.0 |
| Na$_2$O (% by weight) | 0.47 |
| K$_2$O (% by weight) | 0.66 |
| TiO$_2$ (% by weight) | 0.1 |
| Loss at red heat (2 h 1000° C.) | 25.4 |
| Total (% by weight) | 98.76 | c) Alkaline Activation of Clay Mineral A

When determining the total ion exchange capacity (IUF), it is possible to determine from the concentrations of the ions in the eluate that the Na$^+$ and K$^+$ proportion of the total cation exchange capacity is 32% (Na$^+$: 23%, K$^+$: 9%). From this, an amount of 2% soda required for achieving stoichiometric activation with monovalent ions can be calculated.

The clay material A characterized in table 1 is firstly broken up into pieces of less than 3 cm in diameter. The water content is, where appropriate, adjusted by spraying the broken clay material with water to give a water content of from about 45 to 65% by weight. 350 g of the prebroken clay material A are placed into a mixing apparatus (e.g. a Werner & Pfleiderer mixer) and kneaded for one minute. With the mixing apparatus still running, 2% by weight of solid soda (based on anhydrous clay material A) are then added and the mixture is kneaded for another 10 minutes. If the mixture is not sufficiently smooth, distilled water may be added in order to obtain a sufficiently intense shearing action.

The kneaded mass is divided into small pieces which are dried to a water content of 10±2% in a circulating air dryer at about 75° C. for 2 to 4 hours. The dried material is then ground in a rotary crusher (e.g. a Retsch mill) over a 0.12 mm screen.

Model Proteins Used

The following model proteins were used for studying adsorption of proteins:

α-Chymotrypsin (CHY):

α-Chymotrypsin is a digestive enzyme derived from bovine pancreas. The enzyme has a mass of 25.3 kDa. The isoelectric point is between pH 8.1 and 8.6.

Human Serum Albumin (HSA):

HSA is a globular transport protein used as carrier for fatty acids and amphiphiles from the blood into the surrounding tissue. HSA comprises three domains which in turn consist of 585 amino acids with a total mass of 66.4 kDa. The isoelectric point of the molecule is at pH 4.9.

Alkaline Phosphatase (AP):

Alkaline phosphatase is an unspecific phosphoric acid monoesterase which is present in all species, from E. coli to humans, as a dimer of identical subunits. AP is a metalloprotein containing two Zn$^{2+}$ ions and one Mg$^{2+}$ ion. The AP used in the examples was isolated from calf intestinal mucosa. The isoelectric point is at pH 6.0. The molecular weight of the dimer is 140 kDa.

Example 1

Adsorption of Proteins in the Static System

Equilibration of Clay Materials

In each case 25.0 mg of the above-characterized clay material A are weighed in a 50 ml reaction vessel (Sarstedt AG & Co., Nümbrecht, DE). In each case 10 ml of the sample preparation buffers specified in table 4 are added, and the reaction vessel is treated in an ultrasonic bath for 30 minutes. The reaction vessel containing the suspension is then agitated on a shaker table at 100 rpm and room temperature for one hour. The samples are in each case centrifuged at 4000 g for 10 minutes and the clear supernatant is then removed by pipetting. The sediment is resuspended in 10 ml of double distilled H$_2$O and agitated at 100 rpm for 5 minutes. The suspension is then centrifuged at 4000 g for 10 minutes and the clear supernatant is removed by pipetting. The equilibrated clay material is then dried at 60° C. for 16 hours.

TABLE 4

100 mM buffers used

| | |
|---|---|
| buffer pH 3.0 | 100 mM sodium phosphate buffer |
| buffer pH 4.0 | 100 mM sodium citrate buffer |
| buffer pH 5.0 | 100 mM sodium acetate buffer |
| buffer pH 6.0 | 100 mM MES buffer |
| buffer pH 7.0 | 100 mM Tris buffer |
| buffer pH 8.0 | 100 mM Tris buffer |
| buffer pH 9.0 | 100 mM Tris buffer |

Preparation of Model Proteins

Stock solutions having a concentration of 2 mg/ml are prepared in double distilled H$_2$O for each of the model proteins. The protein solutions are diluted with the 100 mM buffers of pH 3 to 8, specified in table 4, in a 1:1 ratio to give a total volume of 20 ml.

Generation of Calibration Curves for Determining Protein Concentrations by UV Spectrophotometry Spectrophotometric quantification of proteins is based on measuring UV absorbance of the aromatic amino acids tyrosine (phenol group, 275 nm), tryptophan (indole group, 279 nm) and, to a lesser extent, phenylalanine (257 nm) at 280 nm. Depending on the amino acid composition, concentrations of between 20 and 3000 μg·ml protein may be detected.

In order to determine an unknown protein concentration, absorbance at 280 nm is first determined for a calibration series of solutions of known protein concentration. The unknown protein concentration can be calculated from the linear relationship between absorbance and protein concentration.

For spectrophotometric quantitative evaluation, serial standards of the model proteins are prepared in the 50 mM buffers of the corresponding pH values, specified in table 5. The standards are incubated at 4° C. and 100 rpm on a shaker table for 3 hours. After said incubation, the samples are centrifuged at 4000 g for 10 minutes, and the extinction of the clear supernatant is determined. A calibration curve is established from the data determined.

TABLE 5

| 50 mM buffers used | |
| --- | --- |
| buffer pH 3.0 | 50 mM sodium phosphate buffer |
| buffer pH 4.0 | 50 mM sodium citrate buffer |
| buffer pH 5.0 | 50 mM sodium acetate buffer |
| buffer pH 6.0 | 50 mM MES buffer |
| buffer pH 7.0 | 50 mM Tris buffer |
| buffer pH 8.0 | 50 mM Tris buffer |
| buffer pH 9.0 | 50 mM Tris buffer | a) Examination of pH Dependence of Protein Adsorption

In each case 20 ml of the model protein solution prepared as described above are added to in each case 25 mg of the equilibrated clay material. The samples are incubated on a shaker table at 4° C. and 100 rpm for 3 hours. After said incubation has ended, the samples are centrifuged at 4000 g for 10 minutes. The concentration of the model proteins in the sample supernatants is determined spectrophotometrically at 280 nm against the serial standard of said protein in the relevant buffer. The load of the clay materials is calculated from the difference in protein concentration in the supernatant before and after incubation, as well as the mass of the clay material and the volume of the protein solution. The results of the measurements are plotted as averages of duplicates against the pH values in FIG. 1. For all model proteins, the load of clay material A is highest in citrate buffer at pH 4.

b) Recording of Protein Absorbance Therms

Recording of adsorption isotherms is studied by way of the equilibrium load of clay material A as a function of the model protein concentration in the supernatant.

The experiments are carried out for the particular model proteins at pH 4 in a 50 mM citrate buffer. This corresponds to the conditions under which the maximum had been determined when examining protein adsorption as a function of pH.

To record the adsorption isotherms, first a stock solution of the model protein in question with a protein content of 3 mg/ml in 50 mM citrate buffer is prepared. The protein stock solution is then diluted with 50 mM citrate buffer according to the protocol specified in table 6.

TABLE 6

Protocol of diluting protein stock solutions for recording protein adsorption isotherms

| Experiment No. | Protein stock solution volume [ml] | Buffer volume [ml] | c(Protein) [mg · ml$^{-1}$] | Protein/adsorbent mass ratio |
| --- | --- | --- | --- | --- |
| 1 | 2 | 33 | 0.17 | 0.24 |
| 2 | 5 | 30 | 0.43 | 0.60 |
| 3 | 8 | 27 | 0.69 | 0.96 |
| 4 | 12 | 23 | 1.03 | 1.44 |
| 5 | 16 | 19 | 1.37 | 1.92 |
| 6 | 20 | 15 | 1.71 | 2.40 |
| 7 | 24 | 11 | 2.06 | 2.88 |

The diluted solutions of the model proteins are then added in each case to 25 mg of clay material A equilibrated with 50 mM citrate buffer, as described above.

To determine the model protein concentration, a serial standard of each model protein is prepared in a 50 mM citrate buffer. The samples and the standard solution are incubated on a shaker table at 4° C. and 100 rpm for 3 hours and then centrifuged at 4000 g for 10 minutes.

A calibration curve is generated by determining the extinction of the protein serial standards. The load of the clay materials is determined by spectrophotometrically quantifying the proteins in the supernatant of the centrifuged samples. The data are depicted as averages of duplicates in FIG. 2.

Example 2

Adsorption of Proteins in the Dynamic System

Equilibration of Clay Materials

In each case 100 mg of clay material A are suspended with in each case 1 ml of the 50 mM buffers specified in table 5 in a 1 ml Eppendorf tube, and the suspension is pipetted using a pipette into a chromatographic column closed at the bottom with a plug (15×50 mm with 10 µm PTFE stopper). The second column endpiece is attached, and the column is connected to an FPLC apparatus in such a way that the mobile phase flows through it from the bottom to the top. The FPLC pump is adjusted to the flow rate for which the capacity of the adsorbent is to be determined. The movable plug of the column is slowly tightened by hand during equilibration with 20 ml of 50 mM buffer and then loosened by a quarter turn of the screw.

Determination of Protein Binding Capacity 25 ml of a solution of the particular protein in 50 mM citrate buffer are pumped with variable flow rates through a column packed with 100 mg of clay material A. The protein content in the flow-through is determined spectrophotometrically at 280 nm against a serial standard of the model protein in a 50 mM citrate buffer. The flow rate-dependent model protein loads determined for clay material A are depicted in FIG. 3 as averages of duplicates.

Example 3

Elution of Human Serum Albumin

HSA bound to clay material A is eluted using 2 different buffers. All chromatographic steps are carried out at a flow rate of 1 ml/min.

Elution buffer 1: 50 mM citrate, 1M NaCl in double distilled $H_2O$, pH 4

Elution buffer 2: 50 mM $Na_2HPO_4$ in double distilled $H_2O$, pH 7.2

100 mg of clay material A are loaded in flow-through mode with 25 ml of an HSA solution having a concentration of 1 mg/ml in 50 mM citrate buffer, pH 4. After loading, the column is rinsed with 20 ml of 50 mM citrate buffer, pH 4. HSA is eluted by passing 35 ml of elution buffer through the column. The protein content of the flow-through, of the washing and the elution fractions is determined spectrophotometrically at 280 nm. The results for both elution buffers are listed in table 7 as averages of duplicates.

TABLE 7

Protein contents in flow-through, washing and elution fractions of HSA elution from clay material A with 2 different elution buffers

| | HSA content [mg] | | | |
| --- | --- | --- | --- | --- |
| Buffer | Flow-through | Washing fraction | Elution fraction | Elution [% load] |
| Elution buffer 1 | 15.5 | 1.7 | 2.1 | 31 |

TABLE 7-continued

Protein contents in flow-through, washing and elution fractions of HSA elution from clay material A with 2 different elution buffers

| Buffer | HSA content [mg] | | | |
| --- | --- | --- | --- | --- |
| | Flow-through | Washing fraction | Elution fraction | Elution [% load] |
| Elution buffer 2 | 15.4 | 1.7 | 7.0 | 89 |

Three times as much protein was eluted with elution buffer 2 in comparison with elution buffer 1.

The invention claimed is:

1. A method for separating proteins from liquid media, comprising
providing a liquid medium containing proteins,
providing a clay material which has:
a specific surface greater than 150 m$^2$/g,
a pore volume greater than 0.35 ml/g,
an ion exchange capacity greater than 40 meq/100 g, and
a sediment volume in water of less than 15 ml/2 g,
equilibrating said clay material to a pH of from 3.5 to 9.0,
treating said liquid medium with the equilibrated clay material, and
separating the purified, protein-depleted liquid medium from the clay material.

2. The method as claimed in claim 1, wherein the clay material has an $Al_2O_3$ content of less than 11%, based on the anhydrous clay material (atro).

3. The method as claimed in claim 1, wherein the clay material has an $SiO_2$ content of greater than 65% by weight, based on the anhydrous clay material (atro).

4. The method as claimed in claim 1, wherein at least 40% of the pore volume of the clay material are provided by pores having a pore diameter of at least 14 nm.

5. The method as claimed in claim 1, wherein the sediment volume of the clay material is less than 15 ml/2g, after said clay material has been left in water at room temperature for 3 days.

6. The method as claimed in claim 1, wherein the clay material has not been subjected to any surface activation with acid.

7. The method as claimed in claim 1, wherein the clay material is equilibrated with a buffer.

8. The method as claimed in claim 7, wherein the buffer concentration is within a range from 30 to 100 mmol.

9. The method as claimed in claim 1, wherein the clay material has been activated by treatment with an alkali metal-containing compound.

10. The method as claimed in claim 1, wherein the proteins are removed by passing the liquid medium through a filter packing comprising the clay material.

11. The method as claimed in claim 1, wherein the proteins are removed by passing the liquid medium through a chromatography column whose packing comprises the clay material.

12. The method as claimed in claim 1, wherein the proteins bound to the clay material are eluted with an eluent, after the purified, protein-depleted liquid medium has been removed.

13. The method as claimed in claim 12, wherein the eluent and the liquid medium have a different pH.

14. The method as claimed in claim 1, wherein the clay material has a particle size of >45 μm.

15. The method as claimed in claim 1, wherein the clay material mixture is used together with a further adsorptive material.

16. The method as claimed in claim 15, wherein the further adsorptive material is selected from the group consisting of silica gel, cellulose and polyvinylpyrrolidone.

17. The method as claimed in claim 15, wherein the clay material and the further adsorptive material are in a ratio of between 1:10 and 10:1, based on weight.

18. The method as claimed in claim 2, wherein the clay material has an $SiO_2$ content of greater than 65% by weight, based on the anhydrous clay material (atro).

19. The method as claimed in claim 1, wherein the sediment volume of the clay material is less than 10 ml/2g, after said clay material has been left in water at room temperature for 3 days.

20. The method as claimed in claim 1, wherein the clay material has been activated by treatment with a sodium containing compound.

* * * * *